United States Patent
Gu et al.

(10) Patent No.: US 11,911,536 B2
(45) Date of Patent: Feb. 27, 2024

(54) METHOD FOR MOLDING SELF-SUPPORTING SILK FIBROIN CATHETER STENT

(71) Applicant: SOUTHEAST UNIVERSITY, Jiangsu (CN)

(72) Inventors: Ning Gu, Jiangsu (CN); Xin Liu, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 364 days.

(21) Appl. No.: 17/602,202

(22) PCT Filed: Sep. 23, 2020

(86) PCT No.: PCT/CN2020/117010
§ 371 (c)(1),
(2) Date: Oct. 7, 2021

(87) PCT Pub. No.: WO2021/068743
PCT Pub. Date: Apr. 15, 2021

(65) Prior Publication Data
US 2022/0211920 A1   Jul. 7, 2022

(30) Foreign Application Priority Data
Oct. 8, 2019   (CN) .......................... 201910948846.0

(51) Int. Cl.
*A61L 31/00* (2006.01)
*A61L 31/04* (2006.01)
*B29C 39/38* (2006.01)
*B29L 31/00* (2006.01)

(52) U.S. Cl.
CPC ............ *A61L 31/047* (2013.01); *B29C 39/38* (2013.01); *B29K 2089/00* (2013.01); *B29L 2031/7542* (2013.01)

(58) Field of Classification Search
CPC ......... A61L 31/00; A61L 31/04; A61L 31/047
See application file for complete search history.

(56) References Cited

U.S. PATENT DOCUMENTS

2012/0123519 A1* 5/2012 Lovett ................... A61L 27/227
                                                              264/171.12
2019/0167843 A1* 6/2019 Rodrigues De Carvalho ..............
                                                              A61L 27/56

FOREIGN PATENT DOCUMENTS

| CN | 1742690 A | 3/2006 |
|---|---|---|
| CN | 102133432 A | 7/2011 |
| CN | 102397582 A | 4/2012 |
| CN | 102488929 A | 6/2012 |
| CN | 104971386 A | 10/2015 |
| CN | 105963790 A | 9/2016 |
| CN | 108404219 A | 8/2018 |
| CN | 109667059 A | 4/2019 |
| CN | 110585480 A | 12/2019 |

OTHER PUBLICATIONS

Zhao, Yahong et al., "Degradation Behaviors of Nerve Guidance Conduits Made up of Silk Fibroin in Vitro and in Vivo", Chinese Master's Theses Full-Text Database, Medicine & Health Sciences, No. 03, Mar. 15, 2012 (Mar. 15, 2012), ISSN:1674-0246, p. 7 paragraph 1, p. 9 paragraphs 2-3, p. 18 paragraph 1; (p. 69).

* cited by examiner

*Primary Examiner* — Jacob T Minskey
*Assistant Examiner* — Matthew Hoover
(74) *Attorney, Agent, or Firm* — Muncy, Geissler, Olds & Lowe, P.C.

(57) ABSTRACT

The present invention relates to a method for molding a self-supporting silk fibroin catheter stent, which comprises preparing an excellent catheter stent by a mold casting and freeze-drying molding process using silk fibroin as a raw material. The raw material is silk fibroin extracted from natural mulberry silk; and the mold is a hollow tubular mold, having an outer shell that is a transparent polyethylene straw with a diameter of 6 mm and an inner core that is a fiber rod FRP with a diameter of 3 mm, with the two ends being closed. The mold casting and freeze-drying molding process comprises the steps of casting; pre-freezing; removing the mold and placing the mold onto a pre-frozen freeze-drying plate; and freeze-drying. The freeze-drying procedure comprises: (1) a pre-freezing stage; (2) a freezing-vacuum transition stage; (3) a gradient temperature-rising and freeze-drying stage; and (4) a secondary freeze-drying stage. The freeze-drying procedure is strictly regulated in accordance with the specifications of freeze-dried stents. The prepared stent has a good shape, and good tolerance without adding any additional components. The stent presents a three-dimensional porous space structure, the process is simple, and the stent meets the requirements for tissue-engineered vascular stent in clinic.

8 Claims, 3 Drawing Sheets

METHOD FOR MOLDING SELF-SUPPORTING SILK FIBROIN CATHETER STENT

TECHNICAL FIELD

The present invention relates to a method for molding a self-supporting silk fibroin catheter stent which is useful in the technical field of vascular tissue engineering.

BACKGROUND

Vascular rupture injury caused by natural disasters, violent attacks, traffic accidents and common vascular diseases is extremely common in clinic. Vascular rupture injury not only leads to serious blood supply insufficiency, causing hemorrhagic shock, hematoma, traumatic pain and other associated diseases, but also brings great psychological and life burden to the patient. Generally, end-to-end sutures can be used directly for defect-free injuries. However, the main treatment for vascular rupture and defect injury is vascular transplantation. Vascular autotransplantation is the gold standard for the treatment of vascular defect injury. However, the source of autologous blood vessels is limited and secondary trauma will be caused. The main solution to this problem in clinic is the use of tissue-engineered vascular grafts. Therefore, the clinical research mainly focuses on vascular grafts as a substitute. Tissue-engineered vascular grafts mainly include three elements including seed cells, growth factors and stents. The stent plays a critical role mainly by providing a microenvironment for blood vessel growth and an adhesion site for cell growth.

Silk fibroin is a natural macromolecular protein which, due to low price, wide variety of sources, good biocompatibility and controllable biodegradability, is widely used in the field of biomedical materials. The material consists essentially of 18 kinds of amino acids. The final degradation products are amino acids and small peptides, which can be easily metabolized in human body, without causing obvious inflammation and immune rejection. Therefore, silk fibroin is a desirable choice for materials of vascular stents. In recent years, vascular silk fibroin stents have also been widely developed and used, and numerous methods for producing silk fibroin vascular stents have also been proposed. At present, commonly used methods for producing silk fibroin vascular stent mainly include freeze drying and electrospinning. Currently, the electrospinning technology has found wide use in the preparation of silk fibroin vascular stents. For example, a nanofiber vascular stent is produced by Han Zhichao et al. by electrospinning (CN102397582A, Apr. 4, 2012); a regenerated tissue engineered silk fibroin stent containing vascular endothelial growth factor is produced by Zhang Yaopeng et al. by electrospinning (CN102488929A, Jun. 13, 2012); and a tissue engineered silk fibroin stent is prepared by Luo Jie et al. by solution spraying (CN109667059A, Apr. 23, 2019). The stents prepared by these methods are mostly two-dimensional film stents. A microporous three-dimensional silk fibroin stent is prepared by Zhu Zhenghua by freeze drying (CN102133432A, 2011-07-27). Although the stent is prepared and formed, the formability is not so good. The tolerance is poor and the addition of organic solvent hexafluoroisopropanol increases the toxic reaction of the stent. At present, the formation is difficult in the preparation of vascular stents by freeze drying. The stent is poorly formed, and has poor tolerance, so it cannot meet the requirements in clinical use.

The present invention aims to optimize the preparation process of the stent before the freeze-drying process and optimize the freeze-drying process. A three-dimensional porous silk fibroin stent with good formability can be obtained without adding any additional components. The regulation of the process is simple, and the preparation process is simple. The present invention has great prospect of application in the preparation of stents by freeze drying in clinic.

SUMMARY

Technical Problem

In view of the poor formability and poor tolerance of the existing freeze-drying technology, an object of the present invention is to provide a method for molding a self-supporting silk fibroin catheter stent without adding any additional components.

Technical Solutions

The present invention provides a method for molding a self-supporting silk fibroin catheter stent, which comprises preparing the self-supporting silk fibroin catheter stent by a mold casting and freeze-drying molding process using silk fibroin as a raw material. The specific preparation steps are as follows:

a. Design of mold structure: The mold has a structure including a sleeve, an inner core and caps. The sleeve is a polyethylene straw having a diameter of 4-6 mm, by which adhesion of a silk fibroin solution can be effectively prevented. The inner core is a fiber rod FRP with a diameter of 2-3 mm. The caps are made of stainless steel, the cap at one end is closed and the cap at the other end is open, and the diameter is consistent with the diameter of the sleeve. The overall shape and size of the mold are designed according to requirements.

b. Preparation of casting solution: Natural mulberry silk is firstly degummed by treatment with a sodium carbonate solution, then dissolved in a ternary solution of $CaCl_2$-EtOH—$H_2O$, dialyzed, and concentrated, for later use.

c. Freeze-drying molding: The solution is casted, and then frozen for 6-24 hrs in a freezer at $-20°$ C. The freeze dryer is started and set at $-40°$ C. to $-35°$ C. in advance. The mold casted with the solution is positioned on a pre-cooled plate, and the stent is freeze dried according to a predetermined freeze-drying procedure.

The specific step of casting the solution in Step b includes (1) weighing natural mulberry silk and adding to a $NaCO_3$ solution with a concentration of 0.5±0.01% (g/ml), heating to 95-100° C., heating for 30-40 min starting from boiling, washing with dd$H_2O$ to remove the dissolved gum, and repeating the above steps 2-3 times to obtain silk fibroin, which is air dried for later use;

(2) weighing the silk fibroin in Step (1) and dissolving in a ternary solution of $CaCl_2$/EtOH/$H_2O$=1:2:8, where the ternary solution is prepared by dissolving anhydrous $CaCl_2$ in dd$H_2O$, and then adding absolute ethanol, slowly adding silk fibroin into the ternary solution in batches and stirring in a magnetic stirrer with heating at 72-75° C., and further stirring for 20-30 min after silk fibroin is completely dissolved to obtain a silk fibroin solution; and (3) transferring the silk fibroin solution of Step (2) to a dialysis bag and dialyzing against dd$H_2O$ for 3-4 days, and then taking out, placing in a container and concentrating to 5-10% on an ultra-clean workbench, for later use.

After the mold casted with the solution in Step c is removed from the freezer a −20° C., the step of removing the mold and transferring the stent to the pre-cooled plate in the freeze dryer needs to be quick, otherwise the solution will be easily melted away.

The predetermined freeze-drying procedure for the stent in Step c follows a strict gradient heating process with a vacuum level of 300-500 mt. A temperature rise of 4-6° C. is one gradient, and each temperature gradient is maintained for 100-200 min.

The predetermined freeze-drying procedure for the stent in Step c includes two freeze-drying steps.

The $NaCO_3$ solution with a concentration of 0.5±0.01% (g/ml) in Step (1) is a solution in $ddH_2O$.

The molecular weight cut-off of the dialysis bag in Step (3) is 12000-14000.

The dialyzing solution in Step (3) is changed 3-5 times a day.

Beneficial Effect

1. The self-supporting silk fibroin catheter stent prepared in the present invention has a three-dimensional porous spatial structure. a large specific surface area, and both hydrophobic and hydrophilic groups, thus being conducive to the cell growth, attachment and proliferation, and providing a good microenvironment for blood vessel growth.
2. The self-supporting catheter stent prepared in the present invention does not contain any additional components, retains the good biocompatibility of silk fibroin, and reduces the inflammation and immune response during use of the catheter.
3. The self-supporting silk fibroin catheter stent prepared in the present invention has good tolerance, and can be stretched by surgical sutures during the repair of the stent.
4. The self-supporting silk fibroin catheter stent prepared in the present invention has a good sustained-release function, and can be used as a slow-release carrier for drugs and factors, etc.
5. The self-supporting silk fibroin catheter stent prepared in the present invention can not only be used in vascular tissue engineering, but also in nerve and skin tissue engineering.

DETAILED DESCRIPTION

Figure 1:
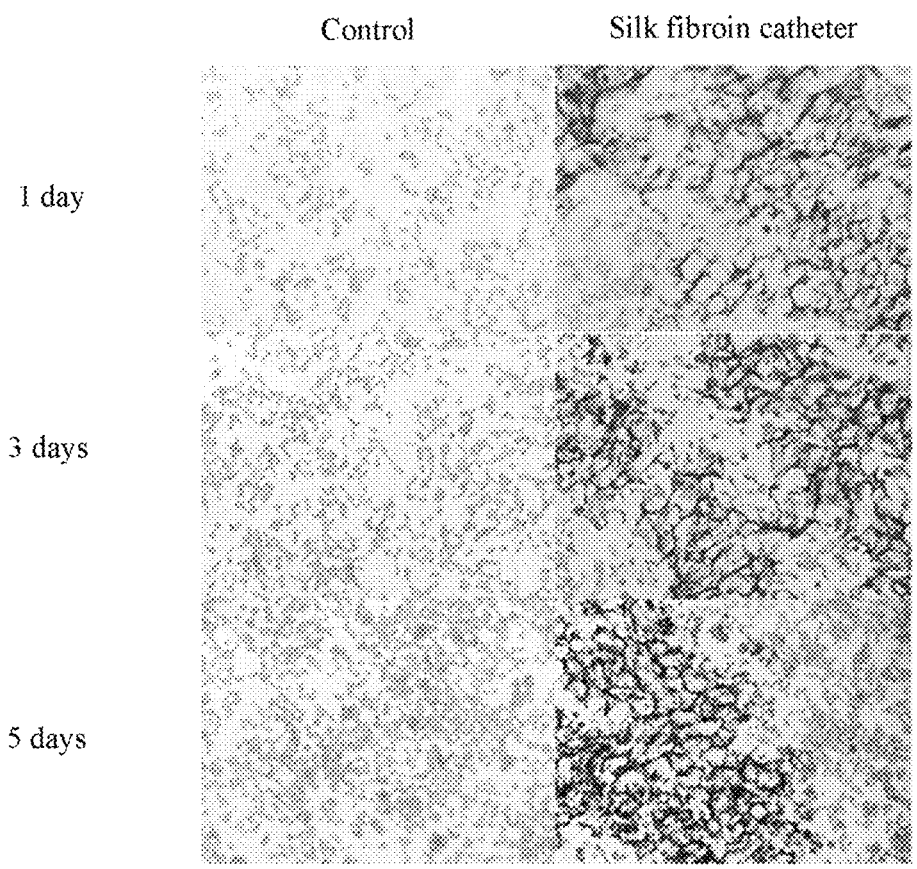
FIG. 1 is a TBO staining diagram of the self-supporting silk fibroin catheter prepared in Example 2 of the present invention co-incubated with human vascular endothelial cells (HUVECs).

The present invention provides a method for molding a self-supporting silk fibroin catheter stent without adding any additional components. The method comprises the following steps:

(1) degumming natural silk by treatment with a sodium carbonate solution to obtain silk fibroin;
(2) dissolving the silk fibroin obtained in Step (1) in a ternary solution to obtain a silk fibroin solution;
(3) dialyzing the silk fibroin solution in Step (2) in a dialysis bag to obtain a dialyzed silk fibroin solution;
(4) concentrating the dialyzed silk fibroin solution obtained in Step (3) in a fume hood, and filtering for later use;
(5) casting the concentrated silk fibroin solution obtained in Step (4) into a catheter mold;
(6) sealing the mold and pre-freezing for 6-24 hrs in a freezer at −20° C.;
(7) starting the freeze dryer until the plate reaches a temperature of −40 to −35° C.;
(8) removing the pre-frozen mold with stent in Step (6), removing the caps at two ends of the mold and the inner core, and positioning the stent on the pre-cooled plate in Step (7); and
(9) freezing the stent in Step (8) following a set cyclic freeze-drying procedure.

The natural silk in Step (1) is mulberry silk, mainly consisting of silk fibroin and sericin at a weight ratio of 17:3-4:1. The silk fibroin is a main component of silk and is composed of 18 kinds of amino acids, where serine (Ser), alanine (Ala) and glycine (Gly) account for about 85% of the total components and are at a molar ratio of 1:3:4. The degumming by treatment with a sodium carbonate solution comprises treating with a basic sodium carbonate solution of 0.5±0.01%; and boiling for 2-3 times and washing with $ddH_2O$.

The ternary solution in Step (2) comprises anhydrous calcium chloride, absolute ethanol and double distilled water at a molar ratio of 1:2:8. The dissolution temperature is 70-75° C. The dissolution time is such that after complete dissolution, the solution is further heated with stirring at this temperature for 30-40 min. The volume ratio of silk fibroin to the solution is 1:4-6.

The molecular weight cut-off of the dialysis bag in Step (3) is 12000-14000. The dialyzing solution is $ddH_2O$, and the dialysis time is 3-4 days. $ddH_2O$ is changed 3-5 times a day.

The fume hood in Step (4) needs to be clean. The content of the solution after concentration is 5-10%. A 50-100 μm nylon filter is used for filtration. The ready-to-use solution is stored in a freezer at 4° C.

The catheter mold in Step (5) has a structure mainly including a sleeve, an inner core and caps. The sleeve is a polyethylene straw having a diameter of 4-6 mm, by which adhesion of a silk fibroin solution can be effectively prevented. The inner core is a fiber rod FRP with a diameter of 2-3 mm. The cap is made of stainless steel, the cap at one end is closed and the cap at the other end is open, and the diameter is consistent with the diameter of the sleeve. The overall shape and size of the mold are designed according to requirements.

The pre-freezing time in Step (6) can also be appropriately extended.

The plate in the freeze dryer in Step (7) is pre-cooled for 120 min or more.

The caps at both ends of the mold and the inner core as described in Step (8) must be removed quickly, to prevent the silk fibroin solution from melting. The stent positioned on the plate needs to be in direct contact with the plate, and is pre-frozen for 40-60 min or more.

The predetermined freeze-drying procedure for the stent in Step (9) follows a strict gradient heating process. The freezing process includes four stages, including a pre-freezing stage; a freezing-vacuum transition stage; a gradient temperature-rising and freeze-drying stage; and a secondary freeze-drying stage. Pre-freezing stage: The pre-freezing temperature is maintained at −40° C. to −35° C., and the time is 300-500 min. Freezing-vacuum transition stage: The freezing temperature is maintained to be the same as that in the pre-freezing stage, and the time is 100-200 min. Gradient temperature-rising and freeze-drying stage: The starting temperature is maintained to be the same as that in the freezing-vacuum transition stage, each temperature gradient is maintained for 100-200 min; and a temperature rise of 4-6° C. is one gradient. Secondary freeze-drying stage: The temperature is 5-10° C. higher than the highest temperature in the gradient temperature-rising and freeze-drying stage, the time is 800 min or more, and the vacuum level of the whole process is 300-500 mT, and maintained to be constant.

To deepen the understanding of the present invention, the present invention is further described in detail below with reference to the embodiments.

Example 1

Step 1: Preparation of Silk Fibroin (Degumming)

40-50 g of the purchased mulberry silk (with sericin) was weighed into a stainless steel pot. Then anhydrous sodium carbonate as solid particles was weighed and dissolved in 2 L of double distilled water. The dissolved sodium carbonate solution (with a concentration of 0.5%) was poured into the stainless steel pot containing mulberry silk. The mulberry silk was fully pressed by a glass rod so that the mulberry silk is completely immersed in the sodium carbonate solution. Then the pot is positioned on an induction cooker and heated until boiling. Starting from boiling, the mulberry silk was taken out after 30 min. For the sake of evenly heating, the mulberry silk was stirred several times during cooking. Then the cooked mulberry silk was washed 3-4 times with double distilled water. At this time, the sericin was removed and silk fibroin was exposed. In order to fully remove the sericin, the above steps were repeated 2 times. Then the cooked silk fibroin was washed several times with double distilled water, until the PH test paper showed neutrality. The silk fibroin was dehydrated, and air dried for later use.

Step 2: Preparation of Silk Fibroin Solution 20 g of solid silk fibroin prepared in Example 1 was weighed into a preservation bag for later use. A 250 ml beaker is prepared, and 37 g of anhydrous calcium chloride was weighed into the beaker. 48 ml of double distilled water, and 40 ml of absolute ethanol were added to fully dissolve it. The resulting solution was stirred evenly in a magnetic stirrer, with a layer of plastic wrap covered on the top of the beaker to prevent ethanol from evaporation and the heating temperature maintained at 72° C. 20 g of solid silk fibroin was added in portions with stirring, and then further stirred for 20-30 min to fully dissolve the silk fibroin. The solution was allowed to cool at room temperature, and was dialyzed in a dialysis bag (molecular weight cut-off: 12000-14000) for 3 days, during which the dialyzing solution (ddH$_2$O) was changed 4 times a day. Finally, the solution was concentrated to 8% in a fume hood, and stored in a freezer at 4° C. for later use.

Step 3: Mold Design and Material Selection

The mold has a structure mainly comprising a sleeve, an inner core and caps. in which the sleeve is a 6 mm straw having a length of 80 mm, by which the problem that the silk fibroin solution cannot be removed after freeze drying due to adhesion to the wall of the sleeve can be effectively prevented. The core is a fiber rod FRP with a diameter of 2 mm, which makes the stent form a tubular structure and is unlikely to adhere to the silk fibroin. A stainless steel cap is provided respectively at two ends. The cap at one end is closed. A wide end of the cap at this end has a diameter of 8 mm, and a height of 5 mm. A narrow end severs to fix the inner core, and has an inner diameter of 2.5 mm, an outer diameter of 4.5 mm, and a height of 6 mm. A small hole is left at a wide end of the cap at the other end, where the small hole has an inner diameter of 2.5 mm an outer diameter of 7 mm, and the inner diameter of the small hole is consistent with the inner diameter of the narrow end fixing the inner core. The outer diameter of a narrow end is 4.5 mm. In order to prevent the leakage of solution from the closed end when the solution is injected, a sealing film is required to seal the closed end.

Step 4: Preparation of Self-Supporting Silk Fibroin Catheter Stent 1.5 ml of the silk fibroin solution prepared in Example 2 was injected into the mold designed in Example 3. Then the mold was placed in a 15 ml centrifuge tube on a test tube rack and pre-frozen in a freezer at −20° C. for 12 hrs. Then the freeze dryer was started until the temperature of the plate was cooled down to −40° C. The frozen silk fibroin was taken out and the caps at the two ends and the inner core of the mold were removed at the fastest speed, such that the silk fibroin does not turn into a mobile phase. The silk fibroin was placed on the plate pre-frozen at −40° C. and maintained for 100 min. The refrigeration was then closed, and a pre-set automatic freeze-drying procedure was started. The procedure includes four stages, including a pre-freezing stage; a freezing-vacuum transition stage; a gradient temperature-rising and freeze-drying stage; and a secondary freeze-drying stage. Program in the pre-freezing stage: freezing temperature −40° C., holding time 300 min, and vacuum level 475T. Freezing-vacuum transition stage: freezing temperature −40° C., holding time 100 min, and vacuum level 300 mT. Gradient temperature-rising and freeze-drying stage: see Table 1. Secondary freeze-drying stage: Temperature 25° C., holding time 1250 min, vacuum level 500 mT, and the sample was taken out after the procedure was completed.

Table 1 shows the procedure of the gradient heating stage of the self-supporting silk fibroin vascular stent prepared in Example 1 of the present invention.

TABLE 1

| Procedure number | Temperature (° C.) | Time (min) | Vacuum level (mT) |
| --- | --- | --- | --- |
| 1 | −40 | 200 | 300 mT |
| 2 | −35 | 200 | 300 mT |
| 3 | −30 | 200 | 300 mT |
| 4 | −25 | 200 | 300 mT |
| 5 | −20 | 200 | 300 mT |
| 6 | −15 | 200 | 300 mT |
| 7 | −10 | 200 | 300 mT |
| 8 | −5 | 200 | 300 mT |
| 9 | 0 | 200 | 300 mT |
| 10 | 5 | 200 | 300 mT |
| 11 | 10 | 200 | 300 mT |
| 12 | 15 | 200 | 300 mT |
| 13 | 20 | 200 | 300 mT |

Example 2: Co-Cultivation of Silk Fibroin Catheter Stent and HUVEC to Observe the Proliferation The silk fibroin catheter prepared in Example 1 was cross-linked with absolute ethanol, to form a water-insoluble structure. Then the silk fibroin catheter was cut to a length of about 5 mm, and placed on a freezing bench for frozen sectioning. The slice collecting means was a small round glass slide coated with PLL for a 24-well culture plate. The thickness of the slice was about 30 μm. Then the glass slide containing silk fibroin was placed on a 24-well culture plate on an ultra-clean workbench, and sterilized by UV overnight. Then 1.5 ml of 75% ethanol was added to each well for disinfection for 30-40 min, and then the plate was washed with the same amount of 0.01 M PBS for at least 3 times for 20 min each time. The plate was naturally air dried and ready for cell inoculation. The cell was HUVEC cells, and a blank control without silk fibroin catheter slice was set. HUVEC cells were inoculated on the material, at a density of $5\times10^4$ cells/well. The cells were incubated in 500 μL of complete medium (containing 45 ml DMEM+5 ml FBS+500 μL double antibody) in an incubator at 37° C. and 5% $CO_2$. The slice was taken out at the scheduled time points of 1, 3, and 5 days. The removed material was gently washed twice with 0.01 M PBS, for about 5 min each time; immobilized in 4% paraformaldehyde for 40 min; and washed 2 times with 0.01M PBS, for about 10 min each time. After washing, a TBO staining solution (Sigma, 0.5 g diluted with PBS 200 ml when used) was added to fully immerse the material. The material was stained for 15 min at room temperature. After staining, the material was washed several times with 0.01M PBS until the slide appeared light blue. Observation of staining under an optical microscope is shown in FIG. 1. (The left column is the blank control group without silk fibroin, the right column is the experimental group containing silk fibroin catheter slices, the top, middle and bottom are the cell proliferation at different time points of 1, 3, and 5 days). The result shows that HUVECs in the experimental group and the control group proliferate well at different time points, and have no significant difference; and the cell morphology is good. The silk fibroin catheter stent has good biocompatibility, which is conducive to cell adhesion and growth.

Figure 2:
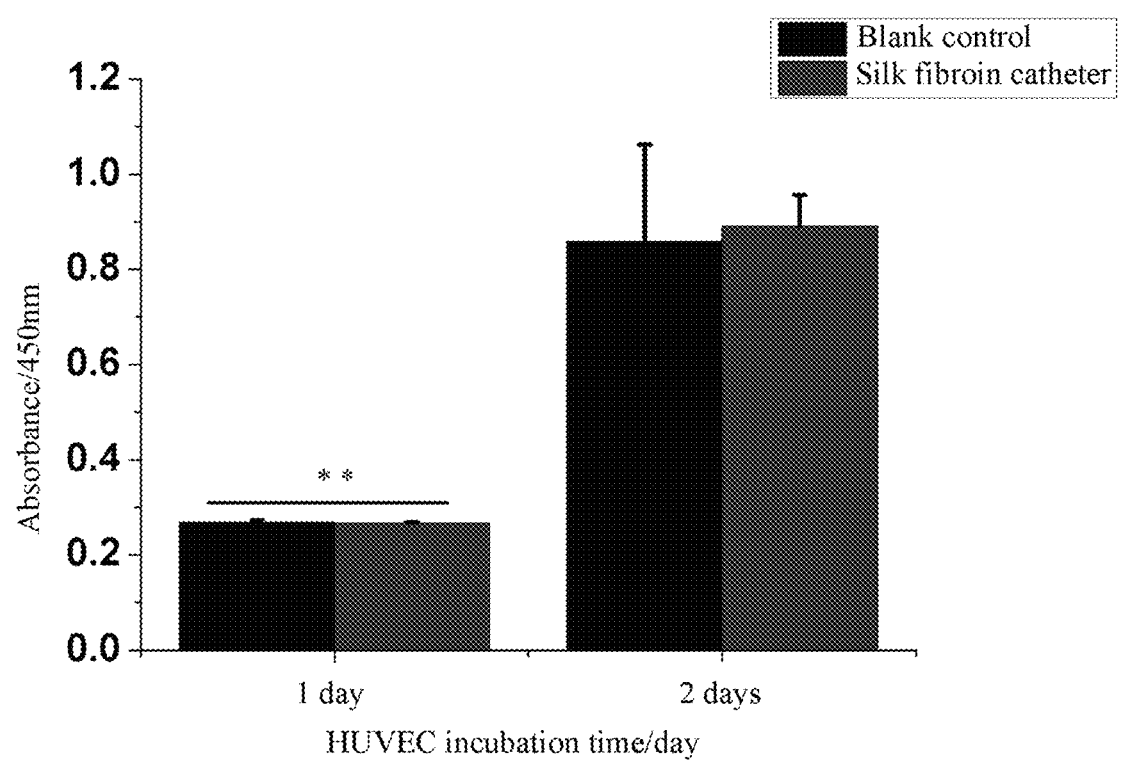
FIG. 2 is a diagram showing the cell viability detected by CCK-8 of human vascular endothelial cells (HUVECs) co-incubated with the self-supporting silk fibroin catheter prepared in Example 3 of the present invention.

Example 3: Co-Cultivation of Silk Fibroin Catheter Stent and HUVEC to Observe the Cell Viability The silk fibroin catheter stent prepared in Example 1 was cross-linked with absolute ethanol, to form a water-insoluble structure. The catheter was cut to a length of 10 mm, and then placed in a 24-well plate. Five replicates were set in each group, and the well without silk fibroin catheter was used as a blank control. The 24-well plate containing the sample was positioned on an ultra-clean workbench, and sterilized by UV overnight. Then 1.5 ml of 75% ethanol was added to each well for disinfection for 30-40 min, and then the plate was washed with the same amount of 0.01M PBS for 5 times. The plate was naturally air dried and ready for cell inoculation. The cells were HUVECs. 1 ml of DMEM medium was added to each well, and incubated for 24 hrs in an incubator at 37° C. and 5% $CO_2$. After incubation, 10% FBS and antibiotics (100 U/ml penicillin and 100 μg/ml streptomycin) were added to the DMEM medium, to obtain a complete medium. Then, HUVEC cells were inoculated on the catheter at a cell density of $1\times10^4$ cells/ml. Finally, the plate was incubated at 37° C. and 5% $CO_2$. After 1 or 2 days, the medium was removed, non-adherent cells were rinsed three times with PBS (0.01M). Subsequently, a mixture of fresh medium and CCK-8 reagent (10:1) was added to the sample, and incubated at 37° C. for 4 hrs under standard culture conditions. Then the suspension (200 μL/well) was transferred to a 96-well plate, and the absorbance at 450 nm was measured on a microplate reader. The result is shown in FIG. 2. The results show that the silk fibroin catheter group is comparable to the control group and shows no obvious difference in the proliferation activity on day 1. On day 2, the proliferation activity of the silk fibroin catheter group is higher that of the control group. This indicates that the silk fibroin catheter has good cell compatibility, and can promote the cell proliferation. The silk fibroin has a three-dimensional structure providing a good microenvironment for cell growth and reproduction. and has the ability to promote the repair of blood vessel damage.

Example 4: Compatibility Test of Silk Fibroin Catheter Stent with Blood

Figure 3:
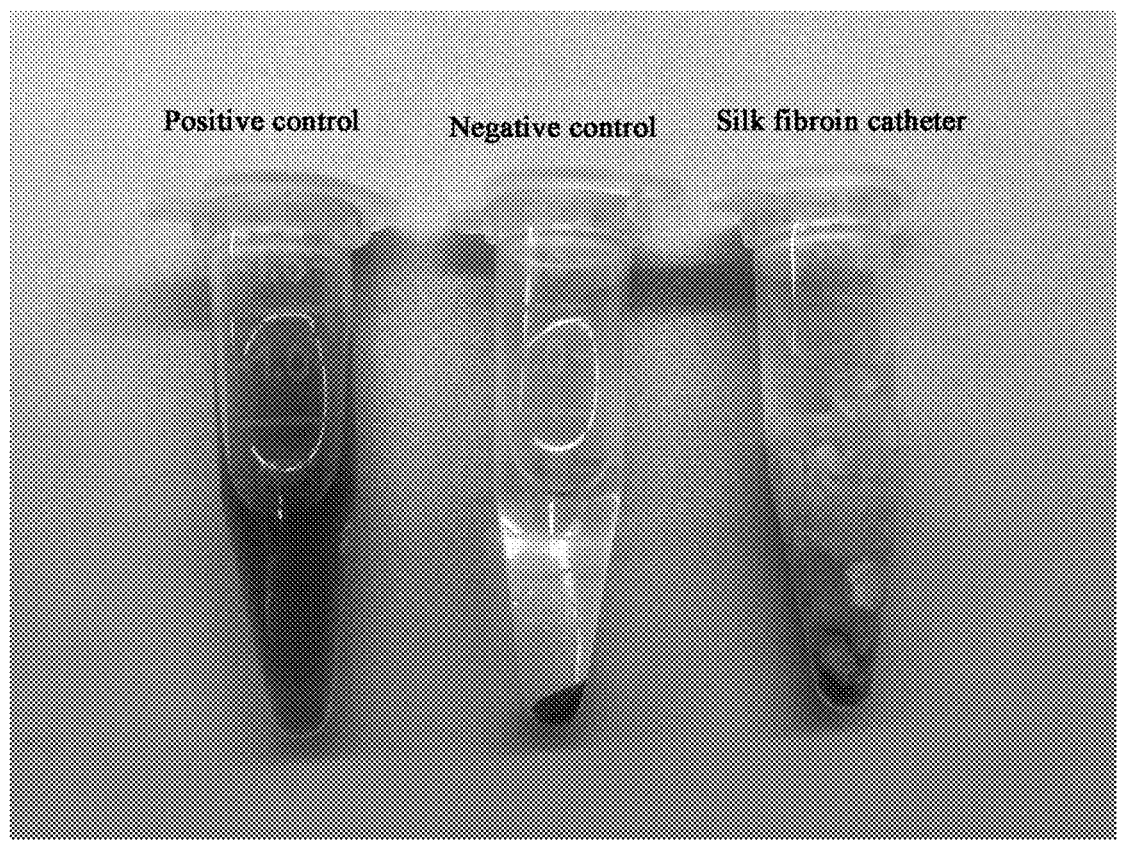
FIG. 3 shows the hemolysis of the self-supporting silk fibroin catheter prepared in Example 4 of the present invention.

The silk fibroin catheter stent prepared in Example 1 was cross-linked with absolute ethanol, to form a water-insoluble structure. 50 mg was weighed for use. Blood was collected from healthy adult Japanese white rabbits (about 2.5 kg/animal) by taking blood from the heart. The Japanese white rabbits were anesthetized with 3% sodium pentobarbital (1.2 ml/kg), and immobilized on an operation table in a supine position. The site corresponding to the heart was shaved and disinfected with iodophor. The site of the most obvious heartbeat was punctured. The needle was pierced into the heart to get the right amount of blood and then pulled out quickly. Then a hemolytic test was carried out. The collected blood was added to an anticoagulation tube, and diluted with 1 physiological saline for later use. 50 mg of the prepared sample was added to a 1.5 ml centrifuge tube, 1 ml of physiological saline was added and allowed to stand at 30° C. for 30 min. 1 ml of distilled water was used as a positive control, and 1 ml of physiological saline was used as a negative control. They were also allowed to stand under the same conditions for 30 min. After that, 100 μL of rabbit blood diluted with physiological saline was added to each centrifuge tube, allowed to stand at 37° C. for 3 hrs, and then centrifuged at 8000 rpm for 5 min. The supernatant was collected and measured for the OD value at 545 nm on a microplate reader. Hemolysis was calculated formula below: Hemolysis %=$(OD_{SF}-OD_{negative})/(OD_{positive}-OD_{negative})\times 100\%$. The results of the study are shown in FIG. 3 and Table 2. The hemolysis rate of the silk fibroin catheter stent is 0.399%, which is much lower than the national standard of 5%. The result shows that the silk fibroin catheter stent had no obvious hemolysis. In other words, the silk fibroin catheter stent has good compatibility with blood.

Table 2 shows the test data of the hemolytic test of the self-supporting silk fibroin vascular stent prepared in Example 1 of the present invention.

TABLE 2

| | Absorbance at 545 nm | | | | |
| --- | --- | --- | --- | --- | --- |
| | Test sample Silk fibroin catheter | Negative control | Positive control | Hemolysis rate-positive rate (%) | Average hemolysis rate (%) |
| 1 | 0.0589 | 0.0555 | 0.9146 | 0.395 | 0.399 |
| 2 | 0.0586 | 0.0553 | 0.9155 | 0.383 | |
| 3 | 0.0593 | 0.0557 | 0.9151 | 0.418 | |

What is claimed is:

1. A method for molding a self-supporting silk fibroin catheter stent, comprising: preparing the self-supporting silk fibroin catheter stent by a mold casting and freeze-drying molding process using silk fibroin as a raw material, wherein the specific preparation steps are as follows:
- a. design of mold structure, wherein the mold has a structure including a sleeve, an inner core and caps, in which the sleeve is a polyethylene straw having a diameter of 4-6 mm, by which adhesion of a silk fibroin solution is effectively prevented; the inner core is a fiber rod FRP with a diameter of 2-3 mm; and the caps are made of stainless steel, the cap at one end is closed and the cap at the other end is open, and the diameter is consistent with the diameter of the sleeve; and the overall shape and size of the mold are designed according to requirements;
- b. preparation of casting solution, wherein natural mulberry silk is firstly degummed by treatment with a sodium carbonate solution, then dissolved in a ternary solution of $CaCl_2$-EtOH—$H_2O$, dialyzed, and concentrated, for later use; and
- c. freeze-drying molding, wherein the solution is casted, and then frozen for 6-24 hrs in a freezer at −20° C.; the freeze dryer is started and set at −40° C. to −35° C. in advance; the mold casted with the solution is positioned on a pre-cooled plate; and the stent is freeze dried according to a predetermined freeze-drying procedure.

2. The method for molding a self-supporting silk fibroin catheter stent according to claim 1, wherein the specific steps of casting the solution in Step b comprises:
- (1) weighing natural mulberry silk and adding to a $NaCO_3$ solution with a concentration of 0.5±0.01% (g/ml), heating to 95-100° C., heating for 30-40 min starting from boiling, washing with $ddH_2O$ to remove the dissolved gum, and repeating the above steps 2-3 times to obtain silk fibroin, which is air dried for later use;
- (2) weighing the silk fibroin in Step (1) and dissolving in a ternary solution of $CaCl_2/EtOH/H_2O=1:2:8$, where the ternary solution is prepared by dissolving anhydrous $CaCl_2$ in $ddH_2O$, and then adding absolute ethanol, slowly adding silk fibroin into the ternary solution in batches and stirring in a magnetic stirrer with heating at 72-75° C., and further stirring for 20-30 min after silk fibroin is completely dissolved to obtain a silk fibroin solution; and
- (3) transferring the silk fibroin solution of Step (2) to a dialysis bag and dialyzing against $ddH_2O$ for 3-4 days, and then taking out, placing in a container and concentrating to 5-10% on an ultra-clean workbench, for later use.

3. The method for molding a self-supporting silk fibroin catheter stent according to claim 1, wherein after the mold casted with the solution in Step c is removed from the freezer a −20° C., the step of removing the mold and transferring the stent to the pre-cooled plate in the freeze dryer needs to be quick, otherwise the solution will be easily melted away.

4. The method for molding a self-supporting silk fibroin catheter stent according to claim 1, wherein the predetermined freeze-drying procedure for the stent in Step c follows a strict gradient heating process with a vacuum level of 300-500 mt; a temperature rise of 4-6° C. is one gradient, and each temperature gradient is maintained for 100-200 min.

5. The method for molding a self-supporting silk fibroin catheter stent according to claim 1, wherein the predetermined freeze-drying procedure for the stent in Step c comprises two freeze-drying steps.

6. The method for molding a self-supporting silk fibroin catheter stent according to claim 2, wherein the $NaCO_3$ solution with a concentration of 0.5±0.01% (g/ml) in Step (1) is a solution in ddH2O.

7. The method for molding a self-supporting silk fibroin catheter stent according to claim 2, wherein the molecular weight cut-off of the dialysis bag in Step (3) is 12000-14000.

8. The method for molding a self-supporting silk fibroin catheter stent according to claim 2, wherein the dialyzing solution in Step (3) is changed 3-5 times a day.

* * * * *